United States Patent [19]
Colin et al.

[11] Patent Number: 5,925,363
[45] Date of Patent: Jul. 20, 1999

[54] COSMETIC COMPOSITION CONTAINING, IN COMBINATION, A SUPEROXIDE-DISMUTASE AND A MELANIN PIGMENT

[75] Inventors: Christian Colin, Paris; Quang Lan N'Guyen, Antony, both of France

[73] Assignee: L'Oreal, Paris, France

[21] Appl. No.: 08/268,620

[22] Filed: Jul. 1, 1994

[30] Foreign Application Priority Data

Jul. 2, 1993 [FR] France .................................. 93 08155

[51] Int. Cl.$^6$ ........................................................ A61K 7/48
[52] U.S. Cl. ................. 424/401; 424/70.1; 424/70.2; 424/70.6; 424/450; 424/520; 514/844; 514/845; 514/846; 514/938; 514/944
[58] Field of Search ................................ 424/401, 450, 424/70.1, 520, 70.2, 70.6; 514/938, 944, 844, 845, 846

[56] References Cited

U.S. PATENT DOCUMENTS 4,129,644  12/1978  Kalopissis et al. ..................... 424/59

FOREIGN PATENT DOCUMENTS 2287899  5/1976  France .

OTHER PUBLICATIONS

Clare et al, Superoxide Dismutase and Chilling INjury in *Chlorella ellipsoidea*, Archives of Biochemistry and Biophysics, vol. 231, No. 1, May 15, pp. 158–163, 1984.

*Primary Examiner*—Jyothsna Venkat
*Attorney, Agent, or Firm*—Nixon & Vanderhye, P.C.

[57] ABSTRACT

Cosmetic, hygienic or dermopharmaceutical composition characterized in that it comprises, in combination, at least one superoxide-dismutase and at least one melanin pigment. In such a composition the melanin pigment reinforces synergistically the action of the SOD against free radicals. Application especially to combating cell aging and to the protection of the skin, of the hair and of the mucosa against the harmful and unaesthetic effects caused by free radicals.

28 Claims, No Drawings

COSMETIC COMPOSITION CONTAINING, IN COMBINATION, A SUPEROXIDE-DISMUTASE AND A MELANIN PIGMENT

The present invention relates to cosmetic, hygienic or pharmaceutical compositions containing a superoxide-dismutase (SOD) used in combination with melanin pigments.

Employed topically, such compositions make it possible in particular to combat cutaneous aging and to protect the skin against the effects of the free radicals induced, for example, by atmospheric pollutants and/or by ultraviolet radiation It is known in fact that the toxicity of atmospheric pollutants, especially of gaseous pollutants such as sulphur dioxide, ozone and nitrogen oxides, is linked with their activity as free radical initiators which are the source of oxidation phenomena causing cell damage in living beings. The cells of organs which are in direct and continuous contact with the external environment, such as the skins the scalp and some mucosa, are particularly sensitive to these effects of gaseous pollutants, which are reflected especially in accelerated aging of the skin, with a complexion lacking in freshness and a premature formation of wrinkles and small creases and also in a decrease in vigor and a dull appearance of hair.

It is known that superoxide-dismutases are enzymes capable of inducing the disproportionation of superoxide ions, according to the reaction.

Many superoxide-dismutases are known.

For example, superoxide-dismutases extracted from ox erythrocytes (Markovitz, J. Biol. Chemo 234 p. 40, 1959) and superoxide-dismutases extracted from *Escherichia coli* (Keele and Fridovich, J. Biol. Chem., 245, p. 61760 1970) have already been described. Superoxide-dismutases extracted from marine bacterial strains, and a process for preparing them, are described in French Patent No. 73.13670 filed on Apr. 16, 1973.

Superoxide-dismutases make it possible in particular to protect the skin and hair especially by maintaining the integrity of the natural keratinous structure; see, for examples French Patent Application No. 75.31354. In addition, superoxide-dismutases improve cutaneous cell respiration and maintain or improve the skin characteristics such as the soft feel, the suppleness and the elasticity. Their presence in hair-care compositions also makes it possible to maintain or to improve the state of the scalps while also protecting the skin of the hands of the person applying these compositions.

Superoxide-dismutases also protect the skin against the inflammation phenomena caused by ultraviolet radiations and against the accelerated aging of the skins especially under the influence of such radiations.

By virtue of these various properties, superoxide-dismutases can be employed in cosmetic compositions for the skin, the hair or the mucosa and in pharmaceutical compositions for dermatological use.

The mechanism of action of superoxide-dismutases may be considered at least partly as being an anti-free radical effect. The superoxide ion $O_2.^-$ (active oxygen) is a radical ion whose instability and reactivity make it a toxic compound because it gives rise to highly damaging hydroxyl free radicals (OH.) especially in the presence of metal ions.

SOD exerts a protective effect especially by trapping the superoxide ions and thus forms a biological defence system against the harmful effects of the free radicals.

It is known, furthermore, that some melanin pigments have already been employed in cosmetic compositions for protecting human epidermis against thee UV, for skin, eyelash and eyebrow makeup or for hair coloring.

It has now been discovered that, surprisingly, the combined use of a superoxide-dismutase (SOD) with melanin pigments makes it possible to reinforce synergistically the anti-radical action exerted by the SOD.

The subject of the invention is very particularly a cosmetic or dermopharmaceutical composition characterized in that it comprises at least one superoxide-dismutase in combination with at least one melanin pigment.

The expression "SOD" is intended to mean SOD enzymes and any equivalent product which has an activity analogous to that of superoxide-dismutases, namely any natural enzyme which can catalyse the disproportionation reaction shown above as well as any product which has this activity, which includes especially modified enzymes such as SODs modified by grafting polyalkoxyalkylenes, polyethylene glycols, polysaccharides or acylated groups, as well as substances containing such products. European Patent Application No. EP 223,257 may be cited in this respect.

SOD enzymes, which are metalloproteins in which the metallic constituent is iron, manganese, copper and/or zinc, may be of various origins.

Particular mention may be made of the SODs of animal origin (for example bovine or porcine), of human origin (for example from placenta or blood), of vegetable origin (for example extracted from fungi, algae, spinach, etc. or those extracted from microorganisms (bacteria or yeasts), or else a recombinant SOD obtained by genetic engineering.

Among the examples of SOD of bovine origin there may be mentioned in particular the SOD of Cu—Zn type which has been purified to homogeneity and approved for clinical applications (New Trends in Allergy, I. Ring et al., Publ. Springer Verlag 1986).

Among the examples of SODs obtained from recombinant cultures of bacteria, yeasts or animal cells there may be mentioned the recombinant human Cu—ZN SOD marketed by the company UBE Industries Ltd.

Among the examples of SODs extracted from bacteria there may be mentioned in particular those extracted from *Escherichia coli* among the superoxide-dismutases extracted from fungi there may be mentioned in particular those extracted from *Pleurotus olearius*; among the superoxide-dismutases extracted from blood there may be mentioned erythrocupreins.

It is also possible to mention superoxide-dismutases extracted from marine bacterial strains such as, for example, strains of *Photobacterium phosphoreum, Photobacterium leiognathi* or *Photobacterium sepia.*

Among the various strains that can be employed there may be mentioned the strains of *Photobacterium phosphoreum* No. ATCC 11040, of *Photobacterium leiognathi* No. ATCC 25521, of *Photobacterium sepia* No. ATCC 15709, of *Escherichia coli* No. ATCC 15224 and of *Pleurotus olearius* Gillet (Paris Cryptogamy Laboratory).

The SODs employed according to the invention can be prepared by application of the methods which have already been described, for example in the paper by Keele et al. (op. cit. and in Eur. J. Rheumatol. and Inflammation, 4, 173–182 (1982).

Superoxide-dismutases extracted from marine bacterial strains can be prepared according to the process described in the abovementioned French Patent Application No. 73.13670.

The SOD employed according to the invention may also be a SOD modified especially according to the teaching of the "International Conference on Medical, Biochemical and Chemical Aspects of Free Radicals" (1988 Kyoto), p. 317, paper by E. Morimoto, or according to the paper by Ando M Yukio p 318 (same source) or else according to documents JP-01250304 (Kanebo) and JP 022731760 The modified SOD described in European Patent Applications EP 424 033 and EP 426 488 may also be mentioned.

The SODs employed according to the invention can furthermore be employed in a form which is stabilized by known techniques, for example with the aid of phosphate, in the presence of alkali metal chloride and of sucrose; see, for example document FR-2,634,125.

The melanin pigments employed in the compositions of the invention are insoluble in the usual solvents, including aqueous solvents.

The melanin pigments which can be employed according to the invention are in particular:

melanin pigments derived from natural or synthetic sources and which can be obtained. (A) by oxidation of at least one indole or indoline compound, or (B) by polymerization, oxidizing or enzymatic, of melanin precursors, or (C) by extraction of melanin from substances which contain it, or (D) by culturing micro organisms.

(A) Firstly, melanin pigments can be obtained by oxidation of at least one indole compound chosen especially from those corresponding to the formula:

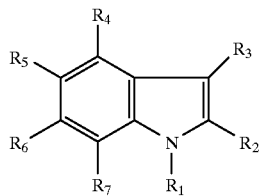

(I)

in which:
R$_1$ and R$_3$ denote, independently of each other, a hydrogen atom or a C$_1$–C$_4$ alkyl group;
R$_2$ denotes a hydrogen atom, a C$_1$–C$_4$ alkyl group, a carboxyl group or an alkoxy(C$_1$–C$_4$)carbonyl group each of the substituents R$_4$ to R$_7$ independently denotes a hydrogen atom, a C$_1$–C$_4$ alkyl group, an —NHR$^0$ or —OZ group, R$^0$ denoting a hydrogen atom, a C$_2$–C$_4$ acyl or C$_2$–C$_4$ hydroxyalkyl group, Z denoting a hydrogen atom, a C$_2$–C$_{14}$ acyl group, a C$_1$–C$_4$ alkyl group or a trimethylsilyl group,
and R$_5$ may additionally denote a halogen atom, it being understood that:
at least one of the substituents R$_4$ to R$_7$ denotes an OZ or NHR$^0$ group, not more than one of the substituents R$_4$ to R$_7$ denoting NHR$^0$ and not more than two of the substituents R$_4$ to R$_7$ denoting OZ and, in this latter case, when Z denotes a hydrogen atom, the two substituents denoting OH are R$_5$ and R$_6$,
and at least one of the substituents R$_4$ to R$_7$ denotes a hydrogen atom and, in the case where only one of these substituents denotes a hydrogen atom, only one of the substituents R$_4$ to R$_7$ then denotes NHR$^0$ or OZ, and the other substituents R$_4$ to R$_7$ then denote a C$_1$–C$_4$ alkyl group or else, if appropriate, in the case of R$_5$, a halogen atom;

as well as the esters or the salts of these compounds. Among these salts particular mention will be made of the addition salts such as hydrochlorides, hydrobromides, sulphates and methanesulphonates and the salts derived from the compounds in which R$_2$ is a carboxylic group, such as the alkali or alkaline-earth metal, ammonium or amine salts. The esters are for example, phosphoric esters.

The indole compounds of formula (I) above are, for example, among 4-hydroxyindole, 5-hydroxyindole, 6-hydroxyindole, 7-hydroxyindole, 4hydroxy-5-methoxyindole, 4hydroxy-5-ethoxyindole, 2-carboxy-5-hydroxyindole, 5-hydroxy-6-methoxyindole, 6-hydroxy-7-methoxyindole, 5-methoxy-6-hydroxyindole, 5,6dihydroxyindole, N-methyl-5,6-dihydroxyindole, 2-methyl-5,6-dihydroxyindole, 3-methyl-5,6-dihydroxyindole, 2,3-dimethyl-5,6-dihydroxyindole, 2-carboxy-5,6-dihydroxyindole, 4-hydroxy-5-methylindole, 2-carboxy-6-hydroxyindole, 6-hydroxy-N-methylindole, 2-ethoxycarbonyl-5,6-dihydroxyindole, 4-hydroxy-7methoxy-2,3-dimethylindole, 4hydroxy-5ethoxy-N-methylindole, 6-hydroxy-5-methoxy-2-methylindole, 6-hydroxy-5methoxy-2,3-dimethylindole, 6-hydroxy-2-ethoxycarbonylindole, 7-hydroxy-3-methylindole, 5-hydroxy-6methoxy-2,3-dimethylindole, 5-hydroxy-3-methylindole, 5-acetoxy-6-hydroxyindole, 5hydroxy-2-ethoxycarbonylindole, 6-hydroxy-2-carboxy-5-methylindole, 6-hydroxy-2-ethoxycarbonyl-5-methoxyindole, 6-N-β-hydroxyethylaminoindole, 4-aminoindole, 5-aminoindole, 7-aminoindole, N-methyl-6-hydroxyethylaminoindole, 6-amino-2,3-dimethylindole, 6-amino-2,3,4,5-tetramethylindole, 6-amino-2,3,4-trimethylindole, 6-amino-2,3,5-trimethylindole, 6-amino-2,3,6-trimethylindole, 5,6-diacetoxyindole, 5methoxy-6-acetoxyindole, 5,6-dimethoxyindole, 5,6-methylenedioxyindole, 5,6-trimethylsilyloxyindole, the phosphoric ester of 5,6-dihydroxyindole, 5,6-dibenzyloxyindole, and the addition salts of these compounds.

5,6-Dihydroxyindole is one of the preferred compounds (I).

The melanin pigments can also be obtained by oxidation of at least one indole compound chosen especially from those corresponding to the formula:

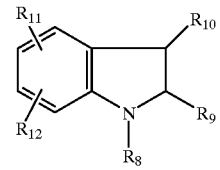

(II)

in which
R$_{10}$ and R$_8$ denote, independently of each other, a hydrogen atom or a C$_1$–C$_4$ alkyl radical,
R$_9$ denotes a hydrogen atom, a C$_1$–C$_4$ alkyl radical or a carboxyl or alkoxy(C$_1$–C$_4$)carbonyl group,
R$_{12}$ denotes a hydrogen atom, a C$_1$–C$_4$ alkyl radical, hydroxyl, C$_1$–C$_4$ alkoxy, amino or C$_1$–C$_{10}$ alkylamino or halogen,
R$_{11}$ denotes a hydrogen atom or a hydroxyl, C$_1$–C$_4$ alkoxy or amino group,
on condition that at least one of the radicals R$_{11}$ and R$_{12}$ denotes a hydroxyl, alkoxy or amino group and on condition that, when $R_{11}$ denotes an amino group, $R_{12}$ cannot denote an alkylamino radical, it also being possible for $R_{11}$ and $R_{12}$ to form a $C_1$–$C_2$ alkylenedioxy group when they are in positions 5 and 6, and their salts or esters.

The compounds corresponding to the formula (II) are chosen particularly from the group consisting of 5,6-dihydroxyindoline, 6-hydroxyindoline, 5,6-methylenedioxyindoline, 7-methoxy-6-hydroxyindoline, 6,7-dihydroxyindoline, 5-hydroxy-4-methoxyindoline, 4,5-dihydroxyindoline, 5-methoxy-6-hydroxyindoline, 4-hydroxy-5-methoxyindoline, 5-hydroxy-6-methoxyindoline, 4,7-dihydroxyindoline, 6-aminoindoline, N-ethyl-4-hydroxyindoline, 1-ethyl-6-aminoindoline, 5,6-diaminoindoline, 1-methyl-6-aminoindoline, 2-methyl-6aminoindoline, 3-methyl-6-aminoindoline, 2-methyl-5,6diaminoindoline, 5-chloro-7-aminoindoline, 3-methyl-5,7diaminoindoline, 5,7diaminoindoline, 2-methyl-5,7-diaminoindoline 7-aminoindoline, 2-methyl-7-aminoindoline, 4-aminoindoline, 4-amino-6-chloroindoline, 4-amino-6-iodoindoline, 4amino-5-bromoindoline, 4-amino-5-hydroxyindoline, 4-amino-7-hydroxyindoline, 4-amino-5-methoxyindoline, 4-amino-7-methoxyindoline, 5-aminoindoline, 2,3-dimethyl-5-aminoindolene, 1-methyl-5-aminoindoline, 2-methyl-5-aminoindoline, 5-N-(1-methylhexyl)aminoindoline, 5,6-dimethoxyindoline and 5,6-dihydroxy-2-carboxyindoline.

In the compounds of formula (II) the $C_1$–$C_4$ alkyl radicals preferably denote methyl, ethyl, propyl, isopropyl, butyl or isobutyl the $C_1$–$C_{10}$ radicals preferably denote methyl, ethyl, propyl, isopropyl, butyl, isobutyl, 1-methylhexyl, 1-methylheptyl or 1-methyloctyl the alkoxy radicals preferably denote methoxy, ethoxy, propoxy or butoxy; halogen preferably denotes bromine, chlorine or iodine.

The salts of the compounds of formula (II) are, in particular, hydrochlorides, hydrobromides, sulphates, methanesulphonates or alkali, alkaline-earth metal, ammonium or amine salts.

The oxidation of the indole compound of formula (I) or indoline compound of formula (II) may be performed in an aqueous or water-solvent(s) medium, in air, optionally in the presence of an alkaline agent and/or of a metallic oxidation catalyst such as, for example, the cupric ion.

The reaction medium preferably consists of water and may, where appropriate, consist of a mixture of water and of at least one solvent chosen so that it rapidly dissolves the indole or indoline compound. Among these solvents there may be mentioned, by way of examples, $C_1$–$C_4$ lower alcohols such as ethyl alcohol, propyl or isopropyl alcohol, tert-butyl alcohol, alkylene glycols such as ethylene glycol, propylene glycol, alkylene glycol alkyl ethers such as ethylene glycol monomethyl, monoethyl and monobutyl ethers, propylene glycol and dipropylene glycol monomethyl ethers and methyl lactate.

The oxidation may also be performed with the aid of hydrogen peroxide especially in the presence of an alkaline agent such as, for example, aqueous ammonia, or in the presence of iodide ions, the iodide being (in particular) an alkali or alkaline-earth metal or ammonium iodide.

The oxidation may also be undertaken with the aid of other oxidizing agents such as periodic acid and its water-soluble salts and derivatives, permanganates and dichromates, for example those of sodium or potassium, sodium hypochlorite, potassium ferricyanide, ammonium persulphate, a silver or lead oxide, ferric chloride, sodium nitrite, salts of rare earths in a high oxidation state including especially cerium, and organic oxidizing agents chosen from ortho- and para-benzoquinones, ortho- and para-benzoquinone mono- or diimines, 1,2- and 1,4-naphthaquinonese and 1,2- and 1,4-naphthaguinone mono- or diimines such as defined, for example, in Application EP-A-0 376 776. One of the preferred salts of periodic acid is sodium periodate.

The oxidizing agents can be activated with a pH modifier. An enzymatic oxidation can also be performed.

In all cases an insoluble oxidation product is formed. The insoluble product can be isolated by filtration, centrifuging, freeze-drying or spraying, and then milled or micronized to reach the desired particle size.

(B) The melanin pigments can also originate from the oxidizing or enzymatic polymerization of melanin precursors such as L-tyrosine, L-dopa, catechol and their derivatives.

(C) The melanin pigments can also originate from the extraction of melanin from natural substances such as human hair or cephalopod (squid, octopus) ink, also known by the name of sepiomelanin. These pigments may be purified and milled before use.

(D) The melanin pigments can additionally be obtained by culturing microorganisms producing melanin either naturally or by genetic modification. Methods for preparation of such pigments are described, for example, in Patent Application WO-90 04029.

The melanin pigment may also be in the form of a composite pigment. The melanin pigment may thus be present at the surface of a particulate filler or incorporated in a colored or colorless lamellar or nonlamellar, inorganic or organic particulate filler. For example, the composite pigment may result from the oxidation of at least one compound (I) or (II), mixed with the particulate filler, in a medium which is essentially a nonsolvent for the said filler, or may result from the oxidizing polymerization of the melanin precursor on a particulate filler.

The particulate filler may be any particulate filler employed or capable of being employed in cosmetic composition and having, for example, dimensions smaller than 100 μm.

Such particulate fillers are, for example, nonlamellar inorganic particles.

The nonlamellar inorganic particles employed in this process are, in, particular, inert inorganic particles less than 20,micrometers in particle size. Such particles are especially particles of calcium carbonate, of silica or of titanium oxide.

Such composite melanin pigments deposited on inorganic fillers, and their preparation, are described especially in Patent Application FR-2,618,069.

Using a similar process it is possible to prepare composite melanin pigments with colored inorganic particles which are compatible with use in cosmetic products. "Colored inorganic particles" is the name given here to nonwhite particles, especially particles consisting of metal salts which are insoluble in the cosmetic medium, such as those referred to in the Colour Index under the chapter "Inorganic Colouring Matters" and bearing numbers 77000 to 77947, other than white pigments.

The nonlamellar organic particles which can be employed in the production of the composite pigments are particles of organic or inorganic, natural or synthetic polymers compatible with use in cosmetics, which have, for example, a molecular weight of between 5,000 and 5,000,000. Composite melanin pigments on such polymer particles, as well as their preparation, are described in European Patent Application No. 3790409.

The lamellar particles which can be employed in the production of composite pigments are inorganic or organic particles which are in the form of leaf lets, possibly layered. These leaflets are characterized by a thickness which is smaller than the largest dimension of the particles. For example, the ratio of the largest dimension to the thickness is between 2 and 100. The largest dimension is generally smaller than 50 micrometers. Such composite melanin pigments deposited on lamellar filler are described, together with their preparation, in European Patent Application No. 467,767.

The synergistic combination of the invention finds an application chiefly in the production of cosmetic or dermopharmaceutical compositions intended for combating cutaneous aging and/or protecting the skin, the hair or the mucosa against the harmful and/or unaesthetic effects caused by the free radicals induced especially by atmospheric pollutants and/or by ultraviolet radiation. Such compositions are therefore also a subject of the invention.

In the compositions of the invention the SOD concentration may be, for example, in the range of 40 to 5,000 SOD enzyme units per 100 g of composition, and especially from 300 to 1,500 units. The SOD enzyme unit is defined by McCord and Fridovitch, J. Biol. Chem. 244, 6049 (1969).

The melanin pigments are generally present in a proportion of 0.001 to 1% by weight, and especially of 0.05 to 0.5% by weight.

The compositions according to the invention may contain the SOD and the melanin pigments either as a chief active ingredient or by way of protection against the oxidation of the other ingredients. In the case where the oxidizable ingredient to be protected undergoes an accelerated decomposition in the presence of keratinous fibres and/or of the skin and/or the mucosa, the SOD with the melanin pigment may be stored by themselves, in dilute or concentrated aqueous solution, or it the form of a complex or freeze-dried material and may be added to the other ingredients of the composition only at the time of use.

Similarly, when the SOD and the melanin pigment are employed with the aim of maintaining or improving the characteristics of the skin or of the hair or the mucosa, these substances may be added to the composition only at the time of use.

The compositions according to the invention may therefore be presented in the form of a packaging as a number of parts containing, on the one hand, the SOD with the melanin pigment and, on the other hand, the other ingredients of the composition. As indicated above, the SOD and the melanin pigment may be stored, for example, in the form of aqueous solution, of complex or of freeze-dried material.

The compositions for the skin according to the invention may contain, besides the binary SOD and melanin pigment combination, active ingredients or excipients usually employed in cosmetic or dermopharmaceutical formulations, such as surfactants, colorants, perfumes, preserving agents, emulsifiers, liquid carriers such as water, fatty substances intended to form the fatty phase of emulsions (such as milks or creams), resins and the like. The compounds intended to form a fatty phase are, for example, mineral or organic, vegetable or synthetic oils, waxes, fatty alcohols or fatty acids.

Liquid paraffin may be mentioned, for example, among inorganic oils and, among synthetic oils, ethyl and isopropyl palmitates, alkyl myristates such as isopropyl, butyl or cetyl myristate, hexyl stearate, triglycerides of octanoic and decanoic acids (for example the product sold under the name "MIGLYOL®" by the company Dynamit-Nobel), cetyl ricinoleate, stearyl octanoate (purcellin oil) and hydroxylated polyisobutene octanoate.

Among the vegetable oils there may be mentioned, for example, sweet almond oil, avocado oil, coconut oil, wheatgerm oil, corn oil, castor oil, olive oil, palm oil, sesame oil, soya oil, argan oil, evening primrose oil, borage oil, essential oils and vegetable waxes such as beeswax or else synthetic waxes such as silicone waxes.

Among fatty alcohols there may be mentioned cetyl alcohol, stearyl alcohol, myristyl alcohol, hydroxystearyl alcohol, oleyl alcohol, isostearyl alcohol, lauryl alcohol, hexadecyl alcohol, ricinoleyl alcohol, behenyl alcohol, erucyl alcohol and 2-octyl-dodecanol.

Among the fatty acids there may be mentioned stearic acid, myristic acid, palmitic acid, oleic acid, linoleic acid, lauric acid, isostearic acid, hydroxy-stearic acid, linolenic acid, ricinoleic acid, arachidic acid, behenic acid, erucic acid and lanolinic acids.

The compositions according to the invention which are intended for a topical application are especially solutions or dispersions of the lotion or serum type, emulsions of liquid or semiliquid consistency of the milk type, which are obtained by dispersing a fatty phase in an aqueous phase (O/W) or vice versa (W/O) or suspensions or emulsions of soft consistency of the cream or gel type, or else microgranulates, or vesicular dispersions of ionic and/or nonionic type.

The compositions of the invention are more particularly packaged compositions, that is to say compositions arranged in an appropriate container which is itself optionally arranged in an individual package.

These compositions are prepared by the usual methods. They form especially cleansing creams for protecting or care of the face, the hands or the body (for example day creams, night creams, makeup removal creams, foundation creams, sun creams), fluid foundations, makeup removal milks, body protection or care milks, sun milks, lotions, gels or mousses for skin care, such as cleansing lotions, sun lotions, artificial tanning lotions, compositions for the bath or deodorizing compositions containing a bactericidal agent.

The compositions according to the invention may also consist of solid preparations forming soaps or cleansing cakes.

The compositions may also be packaged in the form of an aerosol composition also containing a pressurized propellent agent.

The compositions for hair according to the invention may be presented in the form of aqueous, alcoholic or hydroalcoholic solutions or in the form of creams, gels, emulsions, mousses or else in the form of an aerosol composition also containing a pressurized propellent agent.

Besides the conventional active ingredients they may include various adjuvants usually present in these compositions for hair, for example liquid or gel-form carriers, perfumes, dyes, preserving agents, thickening agents and the like.

The synergistic combination according to the invention may be incorporated as a main or secondary ingredient, in various compositions for hair care forming, for example, creams, lotions, gels, serums or mousses for the care of the scalp, shampoos, hairsetting lotions, treating lotions, styling creams or gels, dye compositions (especially oxidation dyes) optionally in the form of dyeing shampoos, restructuring lotions for hair, permanent wave compositions (especially compositions for the first step of a permanent waving), lotions or gels to combat hair loss, and the like.

The compounds of the invention may be especially:
shampoos containing, besides a superoxide-dismutase and the melanin pigments a cationic, anionic or nonionic detergent,
dyeing compositions including coloring shampoos which contain dyes or usual dye precursors,
compositions for the first step (reduction step) of a deformation of hair, containing reducing derivatives such as mercaptans, sulphites and the like,
compositions for slowing down the loss of hair and for promoting fresh growth of hair, containing compounds such as minoxidil (2,4-diamino-6-piperidino-3-pyrimidine oxide) and its derivatives, diazoxide (7-chloro-3-methyl-1,2,4-benzothiadiazine, 1,1-dioxide) and phenytoin (5,5-diphenyl imidazolidine-2,4-dione)

The compositions of the invention are especially compositions free from any oxidizing agent and in particular free from hydrogen peroxide.

The cosmetic composition of the invention may also be for oral and dental use, for example a toothpaste. In this case the composition may contain usual adjuvants and additives for compositions for oral use and especially surface-active agents, thickening agents, moisturizers, polishing agents such as silica, various active ingredients such as fluorides, in particular sodium fluoride, and optionally sweetening agents such as sodium saccharinate.

The cosmetic compositions according to the invention may be both compositions which are ready for use and concentrates which must be diluted before use. The compositions that can be presented in the form of concentrates are, for example, shampoos or compositions for baths.

A further subject of the present invention is a process for cosmetic treatment characterized in that a composition as described above, containing at least one SOD in combination with at least one melanin pigment is applied to the skin, to the hair or to the mucosa.

The cosmetic treatment process of the invention may be implemented particularly by applying the hygienic or cosmetic compositions as defined above using the utilization technique which is conventional for these compositions. For example: application of creams, of gels, of serums, of lotions, of makeup removal milks or antisun compositions to the skin or to the hair, application of a hair lotion to wet hair, shampooing or application of toothpaste to the gums.

The cosmetic treatment process of the invention is implemented so as to apply an effective quantity of the SOD and of melanin pigment, that is to say a sufficient quantity to obtain the desired protection effect.

This cosmetic treatment process is intended in particular to maintain the keratinous structure of the skin or of the hair so as to avoid their degradation and the unaesthetic effects of such a degradation under the influence of the free radicals induced especially by atmospheric pollutants, to maintain or improve the characteristics of the skin (softness, suppleness, elasticity), of the hair or of the mucosa, to protect the skin or the hair against the harmful effects of ultraviolet rays and in particular to treat or prevent the premature aging of the skin.

A further subject of the invention is the use, in combination with a synergistic effect, of at least one SOD and of at least one melanin pigment, as defined above, as active ingredients in the preparation of the cosmetic composition intended to protect the skin or the hair against the effects of the free radicals and/or to treat or prevent the premature aging of the skin.

The following examples illustrate the invention. In these examples the proportions shown are percentages by weights

EXAMPLES OF FORMULATION

Example 1

Oil-In-Water Emulsion

| | |
|---|---|
| SOD (sold by the company Pentapharm and assaying at 3.13 U/mg) q.s. 600 units | 0.19 g |
| Melanin pigment obtained by oxidizing polymerization of 5,6-dihydroxyindole in the presence of aqueous hydrogen peroxide and aqueous ammonia | 0.05 g |
| Polyethylene glycol polyoxyethylenated with 50 moles of ethylene oxide | 1.5 g |
| Diglyceryl monostearate | 1.5 g |
| Liquid paraffin | 24 g |

-continued

| | |
|---|---|
| Cetyl alcohol | 2.5 g |
| Triethanolamine q.s. pH 7 | |
| Water q.s. | 100 g |

This emulsion, prepared in the usual manner, can be employed especially as a day cream.

Example 2

Water-In-Oil Emulsion

| | |
|---|---|
| SOD (sold by the company Bio-Technologie and assayed at 8037 U/mg), q.s. 1,000 units | 0.00012 g |
| Melanin pigment (according to Example 1) | 0.1 g |
| Pigments (iron oxides) | 0.5 g |
| Polyglyceryl sesquiisostearate | 4 g |
| White beeswax | 0.5 g |
| Magnesium stearate | 1.5 g |
| Aluminum stearate | 1 g |
| Polyoxyethylenated hydrogenated castor oil (with 7 moles of ethylene oxide) | 3 g |
| Isopropyl palmitate | 10 g |
| Perhydrosqualene | 15 g |
| Water q.s. | 100 g |

This emulsion, prepared in the usual manner, can be employed especially as a care cream.

Example 3

Vesicular Dispersion

| | |
|---|---|
| Nonionic amphiphile* | 0.9 g |
| Sodium acylglutamate HS21 (Ajinomoto) | 0.1 g |
| Glycerine | 3 g |
| SOD (according to Example 1) | 0.08 g |
| Melanin pigment obtained by oxidizing polymerization of 5,6-dihydroxyindole in the presence of aqueous hydrogen peroxide and of aqueous ammonia | 0.1 g |
| Pigments (iron oxide) | 0.5 g |
| Perhydrosqualene | 10 g |
| Methyl para-hydroxybenzoate | 0.2 g |
| Crosslinked polyacrylic acid (CARBOPOL 940 ® -Goodrich) | 0.4 g |
| Triethanolamine q.s. pH = 7 | |
| Water q.s. | 100 g |

*The nonionic amphiphile is a mixture of products corresponding to the following formula:
$C_{12}H_{25}$—[$OC_2H_3(R)$—O—$C_3H_5(OH)$—O]$_n$—H
in which:
n, denoting the statistical number of units, is equal to 2.7, the groups —$OC_2H_3(R)$— denote radicals:

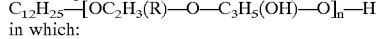

and the groups —$C_3H_5(OH)$—O— denote radicals:

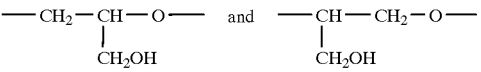

and the groups R denote the radicals $C_{14}H_{29}$ and $C_{16}H_{33}$, statistically as equal molar quantities.

The product sold under the name "ACYLGLUTAMATE HS-21®" is a disodium stearyl glutamate.

This vesicular dispersion is prepared as follows,.

the nonionic amphiphilic compound is added to the cholesterol and to the acylglutamate at a temperature of 100° C.;

the temperature is lowered to 90° C. and the glycerine, the melanin, the pigments and the water are added at this temperature;

the mixture is cooled to 50°, the SOD is added, and then the mixture is homogenized for 2 times 4 minutes with the aid of a Virtis 60 homogenizer (at 40,000 rev/min);

the product obtained is cooled rapidly to ambient temperature and diluted with 20 g of water. The oily phase (perhydrosqualene and methyl para-hydroxy-benzoate) is added and the mixture is then homogenized for 2 times 4 minutes at 40,000 rev/min;

the CARBOPOL gel (CARBOPOL 940® and water q.s. 100 g) is dispersed for 30 seconds at 10,000 rev/min and the whole is then neutralized with triethanolamine.

A smooth and shiny cream is obtained which can be employed especially as a care cream.

Test for inhibition of the production of ethylene:

The following are introduced into a Petri dish 32 mm in diameter in the following order:

1.4 ml of 50 mM phosphate buffer (pH=7.4)

100 µl of 200 mM methionine solution,

100 µl of 4 mM ferric chloride solution,

100 µl of the product to be tested,

100 µl of 4 mM EDTA solution,

100 µl of 400 mM NADH solution,

100 µl of 2 mM riboflavin solution.

This dish is then placed on a small aluminum cup and covered with a quartz cell in order to be exposed under UV-A (365 nm) with a dose of 1 J/cm$^2$.

The combination consisting of NADH, riboflavin, ferric chloride and EDTA, subjected to exposure to the UV-A will generate the reduced oxygen species: $O_2.^-$, $H_2O_2$ and chiefly the hydroxyl radical OH..

The latter will react with methionine, liberating ethylene, the quantity of which is measured by gas phase chromatography.

The substances studied are introduced with the aid of a micropipette. They are:

the SOD (source: Pentapharm assaying at 3.13 U/mg), the melanin pigment: obtained by oxidizing polymerization of 5,6-dihydroxyindole in the presence of aqueous hydrogen peroxide and of aqueous ammonia.

Chromatography conditions: (Varian 3740 model instrument)

injector temperature: 80° C., column temperature: 80° C., detector temperature: 250° C., helium pressure: 36 psi (that is approximately 2.4×10$^5$ Pa), column: 60/80 mesh F1 alumina (source: Supelco), length: 2 m, outer diameter: 1/8.

The results (mean of 3 tests), expressed as percentage decrease in the production of ethylene in comparison with the control (containing 100 µl of phosphate buffer replacing the product to be tested), are summarized in the following table:

TABLE OF RESULTS

| SAMPLE | ETHYLENE % inhibition |
|---|---|
| Control | |
| SOD 0.10% | 59.68 ± 7.53 |
| Melanin pigment 0.10% | 31.14 ± 6.21 |
| SOD + melanin pigment 0.05% + 0.05% | 70.78 ± 4.92 |

Study of these results using one-factor variance analysis shows that they are statistically significant.

The percentages shown are by weight. A content of 0.10 % by weight of SOD corresponds in this case to 313 units of SOD per 100 g of composition.

We claim:

1. A cosmetic, hygienic or dermopharmaceutical composition comprising 40 to 5,000 superoxide dismutase units per 100 g of said composition of superoxide dismutase and 0.001 to 1 percent by weight of a melanin pigment.

2. A process for protecting the skin or hair against the effects of free radicals comprising applying to the skin or hair an effective amount of a composition comprising 40 to 5,000 superoxide dismutase units per 100 g of said composition of superoxide dismutase and 0.001 to 1 percent by weight of a melanin pigment.

3. A process for protecting the skin or hair against the effects of free radicals comprising applying to the skin or hair an effective amount of composition comprising superoxide dismutase and a melanin pigment obtained by oxidizing polymerization of 5,6-dihydroxyindole in the presence of aqueous hydrogen peroxide and aqueous ammonia.

4. A method of combating cutaneous aging comprising applying to the skin or hair an effective amount of a composition comprising 40 to 5,000 superoxide dismutase units per 100 g of said composition of superoxide dismutase and 0.001 to 1 percent by weight of a melanin pigment.

5. A method of combating cutaneous aging comprising applying to the skin or hair an effective amount of a composition comprising superoxide dismutase and a melanin pigment obtained by oxidizing polymerization of 5,6-dihydroxyindole in the presence of aqueous hydrogen peroxide and aqueous ammonia.

6. A cosmetic, hygienic or dermopharmaceutical composition comprising 40 to 5,000 superoxide dismutase units per 100 g of said composition of a product having superoxide dismutase activity and 0.001 to 1 percent by weight of a melanin pigment.

7. A composition according to claim 6 wherein said melanin pigment is an oxidation product or polymerization product of L-tyrosine or L-dopa.

8. A composition according to claim 6 wherein said melanin pigment is extracted from human hair, squid ink or octopus ink.

9. A composition according to claim 6 wherein said melanin pigment is present at the surface of, or incorporated in a particular filler.

10. A composition according to claim 6 wherein said melanin pigment is an oxidation product of an indoline compound having the formula

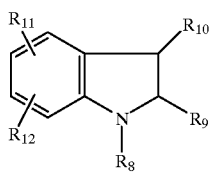

wherein
$R_{10}$ and $R_8$, each independently, represent hydrogen or $C_1$–$C_4$ alkyl,
$R_9$ represents hydrogen, $C_1$–$C_4$ alkyl, carboxyl or alkoxy ($C_1$–$C_4$) carbonyl,
$R_{12}$ represents hydrogen, $C_1$–$C_4$ alkyl, hydroxyl, $C_1$–$C_4$ alkoxy, amino, $C_1$–$C_{10}$ alkylamino or halogen,
$R_{11}$ represents hydrogen, hydroxyl, $C_1$–$C_4$ alkoxyl or amino, or
$R_{11}$ and $R_{12}$ together form a $C_1$–$C_4$ alkylenedioxy, wherein said alkylenedioxy is attached at the 5 and 6 positions,
and an ester or salt of said indole compound,
with the proviso that at least one of said $R_{11}$ and $R_{12}$ represents hydroxyl, alkoxy or amino and that when $R_{11}$ represents amino, then $R_{12}$ is hydrogen, $C_1$–$C_4$ alkyl, hydroxy $C_1$–$C_4$ alkoxyl, amino or halogen.

11. A composition according to claim 6 wherein said melanin pigment is an oxidation product of an indole compound having the formula

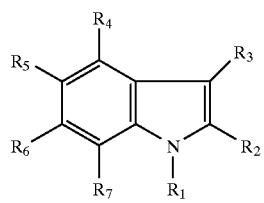

wherein
$R_1$ and $R_3$, each independently, represent hydrogen or $C_1$–$C_4$ alkyl,
$R_2$ represents hydrogen, $C_1$–$C_4$ alkyl, carboxyl or alkoxy ($C_1$–$C_4$) carbonyl,
$R_4$ to $R_7$, each independently, represent hydrogen, $C_1$–$C_4$ alkyl, —NHR$^0$, —OH or —OZ, wherein R$^0$ represents hydrogen, $C_2$–$C_4$ acyl or $C_2$–$C_4$ hydroxyalkyl and Z represents $C_2$–$C_{14}$ acyl, $C_1$–$C_4$ alkyl or trimethylsilyl, and $R_5$ may additionally represents halogen,
with the provisos that
(i) at least one, and not more than one, of $R_4$ to $R_7$ represents said —NHR$^0$,
(ii) at least one, and not more than two of said $R_4$ to $R_7$ represents —OH or
(iii) when two of said $R_4$ to $R_7$ both represent —OH, then said two are $R_5$ and $R_6$,
(iv) at least one of $R_4$ to $R_7$ represents hydrogen, and
(v) when only one of said $R_4$ to $R_7$ represents hydrogen, then only one of remaining $R_4$ to $R_7$ represents NHR$^0$, —OH or OZ and the remaining $R_4$ to $R_7$ represent $C_1$–$C_4$ alkyl or additionally, in the case of $R_5$, halogen, and
an ester or salt of said indole compound.

12. A composition according to claim 11 wherein said melanin pigment is a composite pigment which comprises a melanin pigment present at the surface of a particulate filler or incorporated in a particulate filler.

13. A composition according to claim 11 wherein said melanin pigment is an oxidization product of 5,6-dihydroxyindole.

14. A composition according to claim 6 wherein said melanin pigment is a composite pigment.

15. A composition according to claim 6 wherein said product having superoxide dismutase activity is present in an amount ranging from 40 to 1,500 superoxide dismutase units per 100 grams of said composition.

16. A composition according to claim 6 wherein said melanin pigment is present in an amount in the range of 0.05 to 0.5 percent by weight.

17. A composition according to claim 6 wherein said product having superoxide dismutase activity is present in an amount of 0.05 percent by weight and said melanin pigment is present in an amount of 0.05 percent by weight.

18. A process for protecting the skin or hair against the effects of free radicals comprising applying to the skin or hair an effective amount of a composition comprising 40 to 5,000 superoxide dismutase units per 100 g of said composition of a product having superoxide dismutase activity and 0.001 to 1 percent by weight of a melanin pigment.

19. A process for protecting the skin or hair against the effects of free radicals comprising applying to the skin or hair an effective amount of composition comprising a product having superoxide dismutase activity and a melanin pigment obtained by oxidizing polymerization of 5,6-dihydroxyindole in the presence of aqueous hydrogen peroxide and aqueous ammonia.

20. The process of claim 19 wherein said product having superoxide dismutase activity is present in an amount of 40 to 5,000 superoxide dismutase units per 100 g of said composition and said melanin pigment is present in amount of 0.001 to 1 percent by weight.

21. A method of combating cutaneous aging comprising applying to the skin or hair an effective amount of a composition comprising 40 to 5,000 superoxide units per 100 g of said composition of a product having superoxide dismutase activity and 0.001 to 1 percent by weight of a melanin pigment.

22. A method of combating cutaneous aging comprising applying to the skin or hair an effective amount of a composition comprising a product having superoxide dismutase activity and a melanin pigment obtained by oxidizing polymerization of 5,6-dihydroxyindole in the presence of aqueous hydrogen peroxide and aqueous ammonia.

23. The method of claim 22 wherein said product having superoxide dismutase activity is present in an amount of 40 to 5,000 superoxide dismutase units per 100 g of said composition and said melanin pigment is present in amount of 0.001 to 1 percent by weight.

24. A cosmetic, hygienic or dermopharmaceutical composition comprising 40 to 5,000 superoxide dismutase units per 100 g of said composition of a superoxide dismutase and 0.00 1 to 1 percent by weight of a melanin pigment.

25. A process for protecting the skin or hair against the effects of free radicals comprising applying to the skin or hair an effective amount of a composition comprising 40 to 5,000 superoxide dismutase units per 100 g of said composition of a superoxide dismutase and 0.001 to 1 percent by weight of a melanin pigment.

26. A process for protecting the skin or hair against the effects of free radicals comprising applying to the skin or hair an effective amount of composition comprising a superoxide dismutase and a melanin pigment obtained by oxidizing polymerization of 5,6-dihydroxyindole in the presence of aqueous hydrogen peroxide and aqueous ammonia.

27. A method of combating cutaneous aging comprising applying to the skin or hair an effective amount of a composition comprising 40 to 5,000 superoxide units per 100 g of said composition of a superoxide dismutase and 0.00 1 to 1 percent by weight of a melanin pigment.

28. A method of combating cutaneous aging comprising applying to the skin or hair an effective amount of a composition comprising a superoxide dismutase and a melanin pigment obtained by oxidizing polymerization of 5,6-dihydroxyindole in the presence of aqueous hydrogen peroxide and aqueous ammonia.

* * * * *